(12) United States Patent
Rugnone

(10) Patent No.: US 10,493,421 B2
(45) Date of Patent: Dec. 3, 2019

(54) REACTOR-CONDENSER FOR THE SYNTHESIS OF UREA

(71) Applicant: Casale SA, Lugano (CH)

(72) Inventor: Luca Rugnone, Como (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/754,197

(22) PCT Filed: Jul. 20, 2016

(86) PCT No.: PCT/EP2016/067301
§ 371 (c)(1),
(2) Date: Feb. 21, 2018

(87) PCT Pub. No.: WO2017/032514
PCT Pub. Date: Mar. 2, 2017

(65) Prior Publication Data
US 2018/0243723 A1    Aug. 30, 2018

(30) Foreign Application Priority Data

Aug. 25, 2015 (EP) .................................. 15182263

(51) Int. Cl.
*B01J 19/18* (2006.01)
*B01J 19/00* (2006.01)
*B01J 19/20* (2006.01)
*C07C 273/04* (2006.01)

(52) U.S. Cl.
CPC ....... *B01J 19/1812* (2013.01); *B01J 19/0066* (2013.01); *B01J 19/20* (2013.01); *C07C 273/04* (2013.01); *B01J 2219/00076* (2013.01); *B01J 2219/00768* (2013.01); *B01J 2219/00777* (2013.01); *B01J 2219/00779* (2013.01); *B01J 2219/182* (2013.01); *B01J 2219/185* (2013.01); *Y02P 20/142* (2015.11)

(58) Field of Classification Search
CPC .. B01J 19/1812; B01J 19/0066; B01J 19/006; B01J 4/002; B01J 2219/182; B01J 2219/185; C07C 273/04
See application file for complete search history.

(56) References Cited

U.S. PATENT DOCUMENTS 7,582,795 B2 * 9/2009 Kojima .................. B01D 3/343
422/609
2014/0330040 A1 * 11/2014 Sioli .................... B01J 19/1862
564/72

FOREIGN PATENT DOCUMENTS

EP    2602245 A1    6/2013
WO    01/72700 A1   10/2001

OTHER PUBLICATIONS

International Search Report dated Oct. 12, 2016 in connection with PCT/EP2016/067301.

* cited by examiner

Primary Examiner — Lessanework Seifu
(74) Attorney, Agent, or Firm — Akerman LLP

(57) ABSTRACT

A combined reactor and condenser for the synthesis of urea from ammonia and carbon dioxide, including a condenser section coupled to a reaction section, comprising inputs directed to said condenser section for a gaseous stream comprising ammonia and carbon dioxide and for a solution containing ammonium carbamate and liquid ammonia, and wherein the effluent of the condenser section is sent to the reaction section; the reaction section comprises a plurality of compartments and a plurality of mixers, at least one inside each of said compartments.

11 Claims, 2 Drawing Sheets

REACTOR-CONDENSER FOR THE SYNTHESIS OF UREA

This application is a national phase of PCT/EP2016/067301, filed Jul. 20, 2016, and claims priority to EP 15182263.2, filed Aug. 25, 2015, the entire contents of both of which are hereby incorporated by reference.

FIELD OF THE INVENTION

The invention relates to the field of equipment for the synthesis of urea. The invention relates in particular to a combined reactor-condenser for the synthesis of urea.

Prior Art

Urea is commonly synthesized by reaction of ammonia with carbon dioxide, which involves a fast and highly exothermic step of formation of ammonium carbamate, and a slightly endothermic step of conversion of ammonium carbamate into urea and water.

The reactive system is a vapour-liquid heterogeneous system, where the reactants are progressively transferred from the vapour phase to the liquid phase. It is well accepted that the heat and mass transfer of reactants among the phases are of crucial importance in determining the conversion rate.

The synthesis section of a urea plant typically comprises a urea reactor, a stripper and a condenser forming a high-pressure loop. The reactor produces a solution essentially containing urea, ammonium carbamate, unconverted ammonia and water. This solution is sent to a stripper where the carbamate is decomposed and ammonia is removed at most, possibly with the aid of a stripping medium such as carbon dioxide, obtaining a stripped solution and a gaseous phase containing ammonia and carbon dioxide. Said gaseous phase is then condensed, producing steam usually at a pressure of 3 to 6 bar, and returned to the reactor.

The stripped solution from the high pressure synthesis section is generally sent to a recovery section where water is removed and a flow of recycled carbamate is produced, which is sent back to the high-pressure loop (e.g. to the condenser).

In order to improve the conversion yield, the prior art has focused on the design of the synthesis loop and of the related equipment. It is known, for example, to divide the reactor into compartments by means of perforated plates (so called sieve trays), which allow the dispersion of gaseous CO2 as little bubbles so to maximize the contact area of the gas-liquid system and boost up the mass and heat transfer.

It is also known to combine the functions of the reactor and stripper or condenser into a single equipment.

EP 2 602 245 discloses a combined equipment in the form of a vertical vessel including a first and second separate reaction zones respectively for the formation of ammonium carbamate from ammonia and carbon dioxide and for the conversion of said carbamate into urea and water, and further including a stripping zone.

This reactor however necessitates heat exchange coils to remove heat from the first reaction zone and to furnish heat to the second reaction zone, which are a source of cost since the coils are exposed to an aggressive environment and must be made of an expensive material, e.g. high alloyed steel. Furthermore, the coils reduce the available internal volume and they are very difficult to inspect with the usual non-destructive techniques.

Most modern urea plants use carbon dioxide as stripping medium to maximize the recovery of the unconverted ammonia in the high pressure synthesis.

In the above technology of 002-stripping, the synthesis section is isobaric since the reactor and the stripper operates at same pressure, and the circulation within the high pressure synthesis section is promoted by gravity. In order to provide a static head enough to ensure a stable circulation flow, the equipment must be positioned at different heights leading to a layout which is significantly developed in elevation, typically up to 60 meters, and consequently is expensive. For example the reactor is installed above the stripper requiring an expensive supporting structure. Hence the modern 002-stripping technology still has the drawback of requiring a structure which has an important impact on the global investment cost.

SUMMARY OF THE INVENTION

The aim of the invention is to improve the above mentioned prior art. The invention aims in particular at an efficient and cost-effective layout for the equipment of the high-pressure synthesis loop.

The above aims are reached with a combined reactor and condenser for the synthesis of urea from ammonia and carbon dioxide, comprising a condenser section coupled to a reaction section, comprising at least one input directed to said condenser section for a gaseous stream comprising ammonia and carbon dioxide and for a solution containing liquid ammonia and/or the recycle of ammonium carbamate, and wherein the condensate effluent of the condenser section is sent to the reaction section, characterized in that the reaction section comprises a plurality of compartments, and in that the reaction section comprises a plurality of mixers, including at least one mixer inside each of said compartments.

Said gaseous stream comprising ammonia and carbon dioxide preferably comes from a stripper, particularly a 002-stripper where carbon dioxide is used as a stripping medium.

Said mixers are preferably in the form of rotating impellers. In a preferred embodiment, said impellers are mounted on a common single shaft passing through the reaction section. Said shaft is driven for example by an electrical motor on top of the reactor.

In a preferred embodiment, one of said impellers also provides a thrust to the effluent, so to allow the flow through the reaction section. This impeller can be termed drive impeller. Said drive impeller gives the effluent the head necessary to traverse the reaction section. The provision of said drive impeller is particularly preferred when the reaction section is vertically arranged and hence the effluent must flow upward against gravity.

The head generated by said drive impeller allows the installation of the combined reactor and condenser of the invention at ground level. Accordingly, the invention avoids the expensive installation of the reactor above the other equipment and significantly reduces the costs of the system.

More preferably, said compartments are arranged in series from an input end to an output end of the reaction section, the input end being near said condenser section, and the drive impeller is arranged at the input end of the reaction section. For example in a vertical arrangement the drive impeller is the lowest.

Preferably, said drive impeller, when provided, is also mounted on the common shaft of the other impellers.

According to another preferred embodiment, the reactor comprises an ejector which receives a first input of gaseous stream comprising ammonia and carbon dioxide and a second input of a solution containing ammonia and/or ammonium carbamate, and acts as a phase mixer before entering the condensation section.

Said ejector can also be designed to boost the pressure of said gaseous stream using the energy of the liquid solution. For example the liquid solution is supplied through a high pressure pump and the high pressure pump is designed to deliver the liquid to said ejector at a pressure sufficiently higher than the gaseous stream so that the liquid can be a motive medium for the gas.

In some embodiments, said ejector is accommodated inside the combined reactor-condenser, preferably in the condenser section. An advantage of the accommodation in the condenser section is that the thickness of the ejector body is drastically reduced since it shall not withstand the full pressure against the atmosphere, and the cost is further reduced.

The compartments of the reaction section can be delimited for example by segmental baffles or by trays. A preferred embodiment has four compartments, each equipped with a respective rotating impeller.

The condenser is preferably of the shell-and-tube type, more preferably with U-tubes.

According to various embodiments of the invention, the condenser section and the reaction section can be arranged vertically or horizontally, as will be explained below. The reaction section and the condenser section can be directly coupled to each other. More preferably they are hosted in the same pressure vessel or two pressure vessels connected by a flange.

The invention has the following advantages: the condensation and the synthesis are integrated in a single equipment; the provision of a dedicated mixer in each of the compartments provides that each compartment works as a continuous stirred tank reactor, to the advantage of the heat and mass transfer and then of the conversion yield. The above advantages are reached with simple equipment, without the need of items such as internal coils. The ejector further increases the mixing between the gaseous and liquid phase and in the meantime could boost up the pressure of the gas stream. Furthermore, as mentioned above, the presence of a thrust impeller permits to recover pressure inside the reactor and permits the installation of the equipment at ground level without the need of expensive supporting structures.

An object of the invention is also a plant for the synthesis of urea, according to the attached claims. Preferably the plant is a 002-stripping plant.

DETAILED DESCRIPTION OF PREFERRED EMBODIMENTS

Figure 1:
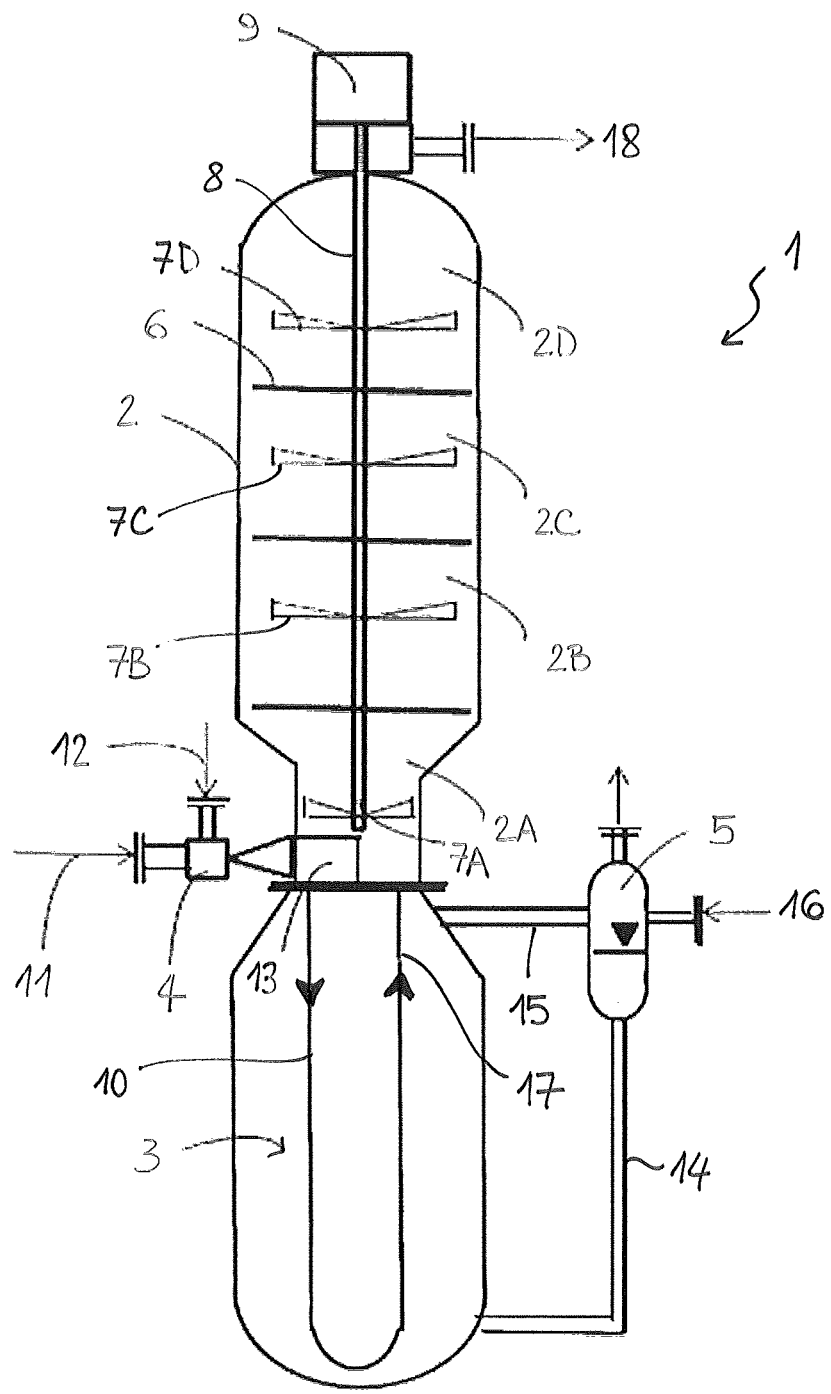
FIG. 1 is a schematic illustration of a combined reactor-condenser for the synthesis of urea according to a first embodiment of the invention.

FIG. 1 is a schematic illustration of a combined reactor-condenser 1 which comprises essentially a reaction section 2, a condensation section 3, an ejector 4 and a tank 5. Both sections 2 and 3 are vertically arranged and the reaction section 2 is above the condensation section 3.

The reaction section 2 includes a plurality of compartments 2A, 2B, 20 and 2D delimited by baffles or trays 6. Each of said compartments has a respective impeller 7A, 7B, 70 and 7D. The impellers are mounted on a common shaft 8 and are powered by a motor 9 installed on top of reactor 1.

The lower impeller 7A, near the condensation section, is designed to give an axial thrust to the fluid, thus providing the motive force for the upward flow through the vertical reaction section 2.

The condensation section 3 comprises a bundle of U-tubes 10. Only one tube is shown in the figure for clarity.

The ejector 4 receives a first input flow 11 of gaseous carbon dioxide and ammonia (for example from a stripper) and a second input flow 12 of ammonia and recycled carbamate (which comes for example from a recovery section). Typically the gas flow 11 has a pressure of 130 to 160 bar and a temperature of 100 to 200° C.; the carbamate flow 12 has a pressure of 150 to 250 bar and a temperature of 30 to 100° C.

The ejector 4 intimately contacts the gas flow 11 and liquid flow 12 to achieve an output flow which is a two-phase mixture where the gas is completely dispersed into the liquid (dispersed flow). Said two-phase mixture is directed into the tubes of the tube bundle 10 by means of a feeding partition 13. The ejector 4 also boosts the pressure of the gas flow 11, using the energy of the liquid flow 12, to facilitate the passage through the bundle 10.

Said two-phase mixture is partially condensed in the tube bundle 10; heat of condensation is used to produce steam 15 which is collected by the steam drum 5. Level of water 14 in the steam drum 15 is controlled by feeding steam condensate 16 when appropriate.

Most of ammonia and carbon dioxide contained in the mixture is converted to carbamate in the tube bundle 10; the conversion is controlled acting on a pressure controller installed in the steam drum 5.

The outlet flow 17 from the tube bundle 10 still contains some ammonia and carbon dioxide in a gas phase. This is due to the presence of passivation air injected along with the stream 11 and also to the need of feeding some gaseous carbon dioxide to the reactor since the heat released by condensation of said carbon dioxide will compensate for the endothermic reaction of dehydration of carbamate.

Said output flow 17 enters the reaction section 2 and traverses the compartments (reaction stages) 2A to 2D. The lower impeller 2A is designed to impart an axial thrust to the flow 17, allowing the upward flow. Each compartment operates as a continuous stirred tank reactor thanks to the respective impeller.

The output of reaction section 2 is a stream 18 which is essentially a solution of urea, water, carbamate and some unconverted ammonia, and is sent to a high-pressure stripper (not shown) which produces the gaseous stream 11.

A separator can be provided to receive the stream 18 and separate gaseous and liquid components. The liquid components are normally sent to the high pressure stripper while the gaseous components can be directed to a scrubber (not shown) to wash the residual ammonia with water rich solution such as the recycle carbamate 12.

Figure 2:
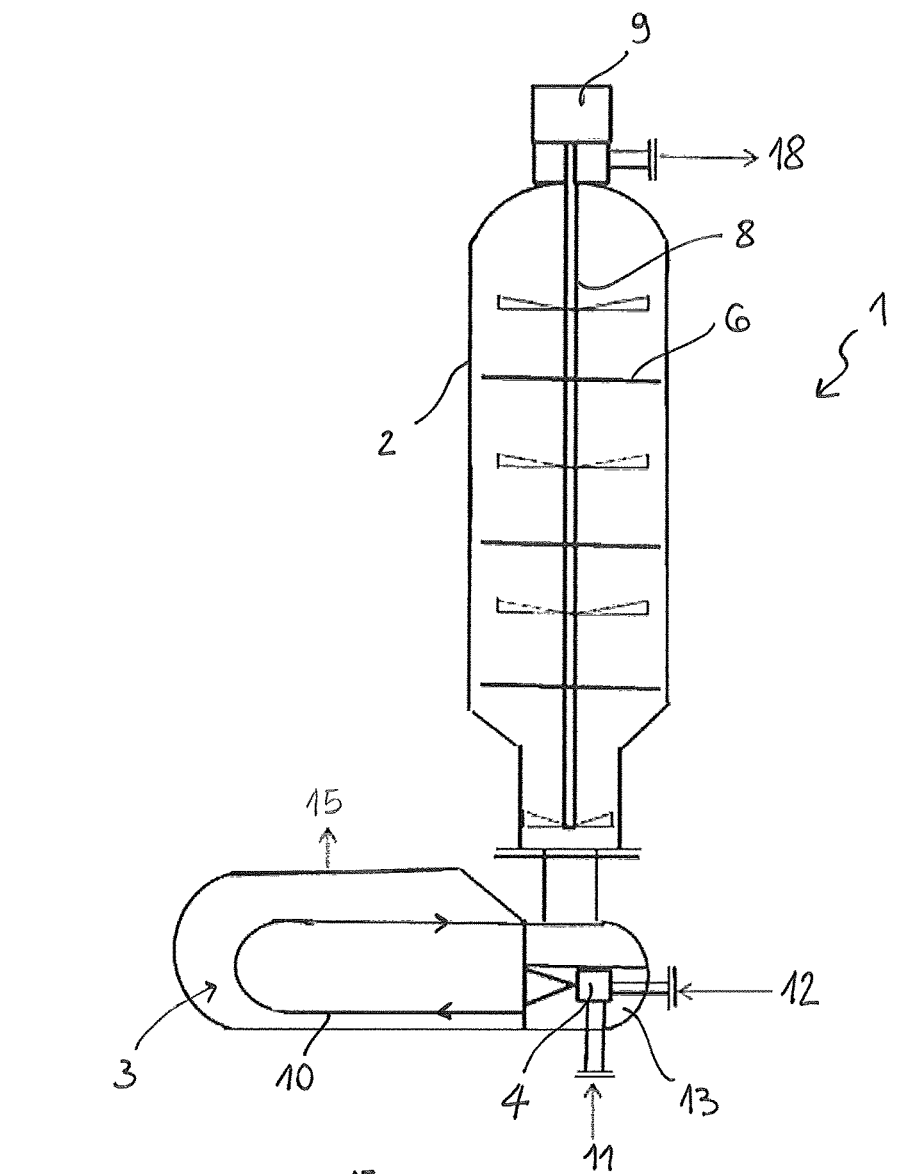
FIG. 2 shows a second embodiment of the invention.

FIG. 2 shows a second embodiment where the condensation section 3 is horizontally arranged. In this embodiment the ejector 4 is located inside the vessel of the condensation section, in the feeding partition 13.

Figure 3:
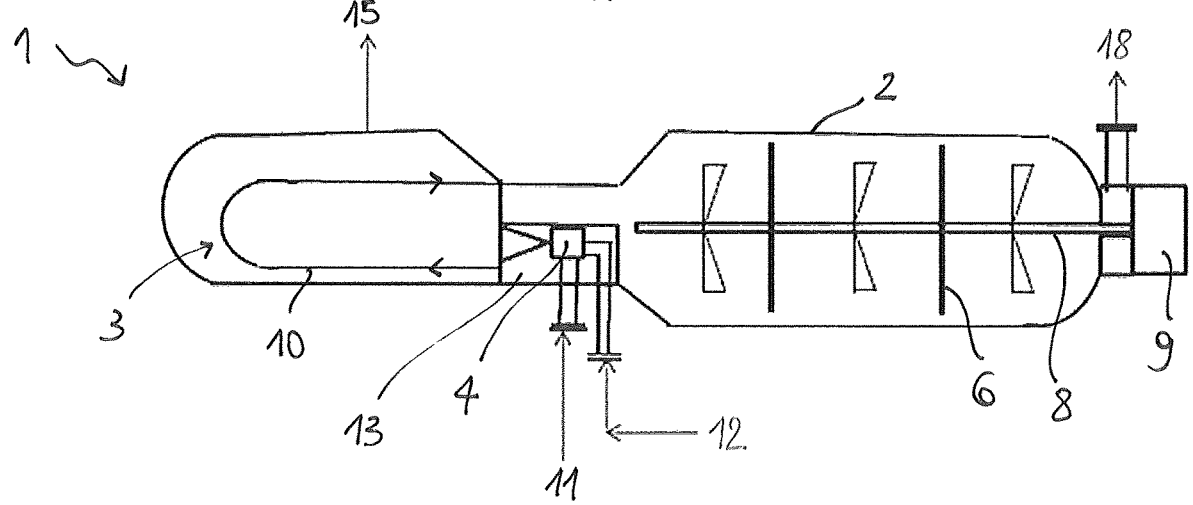
FIG. 3 shows a third embodiment of the invention.

FIG. 3 shows a third embodiment having a horizontal layout of both the reaction section 2 and condensation section 3. In this embodiment the drive impeller 7A can be omitted as the flow through the reactor does not have to overcome the height of the reaction section.

The combined reactor of the invention can be inserted in a urea synthesis loop, for example by connection with a stripper. Hence the invention is useful to new urea plants and also to the revamping of existing plants.

The invention claimed is:

1. A combined reactor and condenser for the synthesis of urea from ammonia and carbon dioxide, including a condenser section coupled to a reaction section, comprising at least one input directed to said condenser section for a gaseous stream comprising ammonia and carbon dioxide, and for a solution containing liquid ammonia and/or ammonium carbamate, and wherein the effluent of the condenser section is sent to the reaction section, characterized in that:
the reaction section comprises a plurality of compartments;
the reaction section comprises a plurality of mixers, including at least one mixer inside each of said compartments;
wherein said mixers are rotating impellers; and
wherein one of said impellers is suitable to impart an axial thrust to said effluent of the condenser section, acting as a drive impeller of the flow through the reaction section.

2. The reactor according to claim 1, said impellers being mounted on a common single shaft passing through the reaction section.

3. The reactor according to claim 1, wherein said drive impeller is also mounted on said common shaft.

4. The reactor according to claim 1, comprising an ejector acting as a phase mixer of said gaseous stream comprising ammonia and carbon dioxide and of said solution containing ammonium carbamate, before entering the condensation section.

5. The reactor according to claim 4, said ejector being designed to boost the pressure of said gaseous stream comprising ammonia and carbon dioxide.

6. The reactor according to claim 1, the reaction section comprising a plurality of segmental baffles or trays to delimit said compartments.

7. The reactor according to claim 1, the reaction section comprising at least four compartments.

8. The reactor according to claim 1, the condenser section being of shell-and-tube type.

9. A reactor according to claim 8, the condenser section comprising a bundle of U-tubes.

10. The reactor according claim 1, wherein the condenser section and the reaction section are arranged according to one of the following:
the condenser section and the reaction section are both vertical, the reaction section being arranged above the condenser section;
the condenser section is horizontal and the reaction section is vertical;
condenser section and the reaction section are both horizontal.

11. A plant for the synthesis of urea from ammonia and carbon dioxide, comprising a synthesis section which includes a stripper and a combined reactor and condenser, said combined reactor and condenser including a condenser section coupled to a reaction section and comprising at least one input directed to said condenser section for a gaseous stream coming from said stripper and comprising ammonia and carbon dioxide, and for a solution containing liquid ammonia and/or ammonium carbamate, and wherein the effluent of the condenser section is sent to the reaction section, wherein:
said reaction section of the combined reactor and condenser comprises a plurality of compartments;
said reaction section comprises a plurality of mixers, wherein said mixers are rotating impellers, including at least one mixer inside each of said compartments;
one of said impellers is suitable to impart an axial thrust to said effluent of the condenser section, acting as a drive impeller of the flow through the reaction section and providing a suitable head for fluid circulation within the synthesis section, and
said combined reactor and condenser is installed at ground level.

* * * * *